(12) United States Patent
Ha et al.

(10) Patent No.: US 10,441,442 B2
(45) Date of Patent: Oct. 15, 2019

(54) BATTERY PACK

(71) Applicant: Samsung Electronics Co., Ltd., Suwon-si, Gyeonggi-do (KR)

(72) Inventors: Taesin Ha, Seongnam-si (KR); ChangHyun Roh, Suwon-si (KR); Youngbo Shim, Seoul (KR); Joon-Kee Cho, Yongin-si (KR); Byung-Kwon Choi, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 806 days.

(21) Appl. No.: 15/000,450

(22) Filed: Jan. 19, 2016

(65) Prior Publication Data

US 2017/0035584 A1  Feb. 9, 2017

(30) Foreign Application Priority Data

Aug. 7, 2015  (KR) .................. 10-2015-0111714

(51) Int. Cl.

| | |
|---|---|
| *A61H 3/00* | (2006.01) |
| *A61F 2/70* | (2006.01) |
| *H01M 2/02* | (2006.01) |
| *A61H 1/02* | (2006.01) |
| *H02J 7/00* | (2006.01) |
| *H02N 2/18* | (2006.01) |

(52) U.S. Cl.
CPC ............. *A61F 2/70* (2013.01); *A61H 1/0244* (2013.01); *A61H 3/00* (2013.01); *H01M 2/0202* (2013.01); *H02J 7/00* (2013.01); *H02N 2/18* (2013.01); *A61H 2201/1207* (2013.01); *A61H 2201/164* (2013.01); *A61H 2201/165* (2013.01); *A61H 2201/1628* (2013.01); *A61H 2201/1676* (2013.01); *A61H 2201/5007* (2013.01); *H01M 2220/30* (2013.01)

(58) Field of Classification Search
CPC ..... A61F 2/70; H02J 7/00; H02N 2/18; A61H 3/00; A61H 2201/165; A61H 2201/1207; A61H 1/0244; A61H 2201/164; A61H 2201/1676; A61H 2201/1628; A61H 2201/5007; H01M 2/0202; H01M 2220/30

See application file for complete search history.

(56) References Cited

U.S. PATENT DOCUMENTS

| | | |
|---|---|---|
| 6,982,497 B2 | 1/2006 | Rome |
| 7,391,123 B2 | 6/2008 | Rome |
| 7,851,932 B2 | 12/2010 | Rome et al. |
| 7,931,178 B2 | 4/2011 | Rome et al. |

(Continued)

FOREIGN PATENT DOCUMENTS

| | | |
|---|---|---|
| JP | 2004-343991 A | 12/2004 |
| KR | 2000-0013652 A | 3/2000 |

(Continued)

*Primary Examiner* — Quang D Thanh
(74) *Attorney, Agent, or Firm* — Harness, Dickey & Pierce, P.L.C.

(57) ABSTRACT

A battery pack including a case, a battery included in the case and relatively movable with respect to the case, a generator attached to the battery and including a generation axis, and a rotation member connected to the generation axis, wherein the rotation member is configured to act a torque enabling the generation axis to be rotatable when the battery is in motion.

18 Claims, 11 Drawing Sheets

(56) References Cited

U.S. PATENT DOCUMENTS

| | | | |
|---|---|---|---|
| 8,564,144 B1 | 10/2013 | Rome et al. | |
| 8,729,747 B2 | 5/2014 | Arnold et al. | |
| 2007/0054777 A1* | 3/2007 | Kawai | A61H 3/00 482/1 |
| 2007/0278902 A1* | 12/2007 | Rastegar | F21L 13/00 310/339 |
| 2008/0164702 A1* | 7/2008 | Brown | F03G 7/08 290/1 E |
| 2013/0197408 A1* | 8/2013 | Goldfarb | A61F 5/0102 601/35 |
| 2015/0346766 A1* | 12/2015 | Justice | G06F 1/163 361/679.03 |
| 2016/0374887 A1* | 12/2016 | Wu | A61F 5/0123 623/31 |

FOREIGN PATENT DOCUMENTS

| | | |
|---|---|---|
| KR | 10-0736204 B1 | 6/2007 |
| KR | 10-0951592 B1 | 4/2010 |
| KR | 2010-0059395 A | 6/2010 |
| KR | 10-1427335 B1 | 8/2014 |

\* cited by examiner

BATTERY PACK

CROSS-REFERENCE TO RELATED APPLICATION

This application claims priority under 35 U.S.C. § 119 to Korean Patent Application No. 10-2015-0111714, filed on Aug. 7, 2015, in the Korean Intellectual Property Office, the entire contents of which are incorporated herein by reference.

BACKGROUND

1. Field

At least one example embodiment relates to a battery pack, and to a motion assistance apparatus including the same.

2. Description of the Related Art

With the onset of rapidly aging societies, more people may experience inconvenience and pain from joint problems, and interest in motion assistance apparatuses enabling the elderly or patients with joint problems to walk with less effort, may increase. Furthermore, motion assistance apparatuses for intensifying muscular strength of human bodies may be useful for a variety of purposes such as, for example, sports or military purposes.

In general, motion assistance apparatuses may include body one or more frames to be disposed on a trunk of a user, one or more pelvic frames to be coupled to lower sides of the body frames to cover the pelvis of the user, one or more femoral frames to be disposed on thighs of the user, one or more sural frames to be disposed on calves of the user, and/or one or more pedial frames to be disposed on feet of the user. The pelvic frames and femoral frames may be rotatably connected by hip joint portions, the femoral frames and sural frames may be rotatably connected by knee joint portions, and/or the sural frames and pedial frames may be rotatably connected by ankle joint portions.

When a motion assistance apparatus is driven, the motion assistance apparatus may use an autonomous battery without support by an external power. When a user is moving, various additional motions take place, in addition to the motion required for movement. Accordingly, the autonomous battery may be charged using the motion of the user.

SUMMARY

Some example embodiments relate to a battery pack.

In some example embodiments, the battery pack may include a case, a battery included in the case and relatively movable with respect to the case, a generator attached to the battery and including a generation axis, and a rotation member connected to the generation axis, wherein the rotation member is configured to act as a torque enabling the generation axis to be rotatable when the battery is moved.

The rotation member may include a connecting body, one end of which is connected to the generation axis and another end of which is to be spaced apart from a center of the generation axis, and an elastic body connected to the other end of the connecting body and the case.

The connecting body may be a torsion spring extended by coiling around the generation axis from the center of the generation axis.

A plurality of elastic bodies may be provided and the plurality of elastic bodies may be radially disposed based on the other end of the connecting body.

The plurality of elastic bodies may be provided and at least one elastic body among the plurality of elastic bodies may have a different spring constant from the remaining elastic bodies.

The elastic body may be provided in four coil springs, and the four coil springs may be substantially orthogonal based on the other end of the connecting body in a balanced condition.

The case may include a supporting member configured to support the battery in order to restrict a movement of the battery in a direction of the generation axis.

The supporting member may surround the generator, and the generator may be relatively movable in the supporting member.

One surface of the battery may be in contact with the case, and another surface of the battery may be in contact with the supporting member.

The battery pack may further include a first bearing disposed between the battery and the supporting member, the first bearing being configured to reduce a frictional force occurring when the battery is moved on a vertical plane relative to the direction of the generation axis, and a second bearing disposed between the case and the battery.

The battery pack may further include a third bearing disposed between the generation axis and the supporting member, the third bearing being configured to reduce a frictional force occurring when the generation axis is in contact with the supporting member.

Other example embodiments relate to a battery pack.

In some example embodiments, the battery pack may include a case including two planes facing each other, a generator attached to any one of the two planes and including a generation axis, a battery disposed on a plane differing from a plane on which the generator is fixed and relatively movable with respect to the case, a connecting body configured to connect a center of the generation axis and the battery at an off-center position, and an elastic body configured to connect the case with the battery, wherein the connecting body is configured to act as a torque enabling the generation axis to be rotatable when the battery is moved.

The battery pack may further include a supporting member in contact with one surface of the battery, the supporting member being configured to restrict a movement of the battery in a direction of the generation axis.

The battery pack may further include a first bearing disposed between the battery and the supporting member, the first bearing being configured to reduce a frictional force between the battery and the supporting member, and a second bearing disposed between a plane of the case and the battery.

Other example embodiments relate to a motion assistance apparatus.

In some example embodiments, the motion assistance apparatus may include a battery pack including a battery movably inserted inside a case, a generator attached to the battery and including a generation axis, and a rotation member configured to connect the generation axis and the case, a driving module powered by the battery pack, a fixing module to which the driving module is attached, the fixing module being attached to a user, a supporting module configured to support a portion of a body of the user and be driven by the driving module, wherein the rotation member is configured to act a torque enabling the generation axis to be rotatable when the battery is moved in response to a motion of the user wearing the motion assistance apparatus.

The rotation member may include a torsion spring, one end of which is connected to the generation axis and another end is to be spaced apart from a center of the generation axis, and at least one coil spring connected to another end of the torsion spring and the case.

The case may include a supporting member configured to be in contact with one surface of the battery and support the battery in order to restrict a movement of the battery in a direction of the generation axis.

A plurality of coil springs may be provided, and at least one coil spring may have a different spring constant from the remaining coil springs, and a resultant force applied by the plurality of coil springs may be in a direction differing from a direction parallel to the generation axis.

Additional example embodiments will be set forth in part in the description which follows and, in part, will be apparent from the description, or may be learned by practice of the example embodiments.

BRIEF DESCRIPTION OF THE DRAWINGS

These and/or other example embodiments will become apparent and more readily appreciated from the following description, taken in conjunction with the accompanying drawings of which.

DETAILED DESCRIPTION

Figure 1:
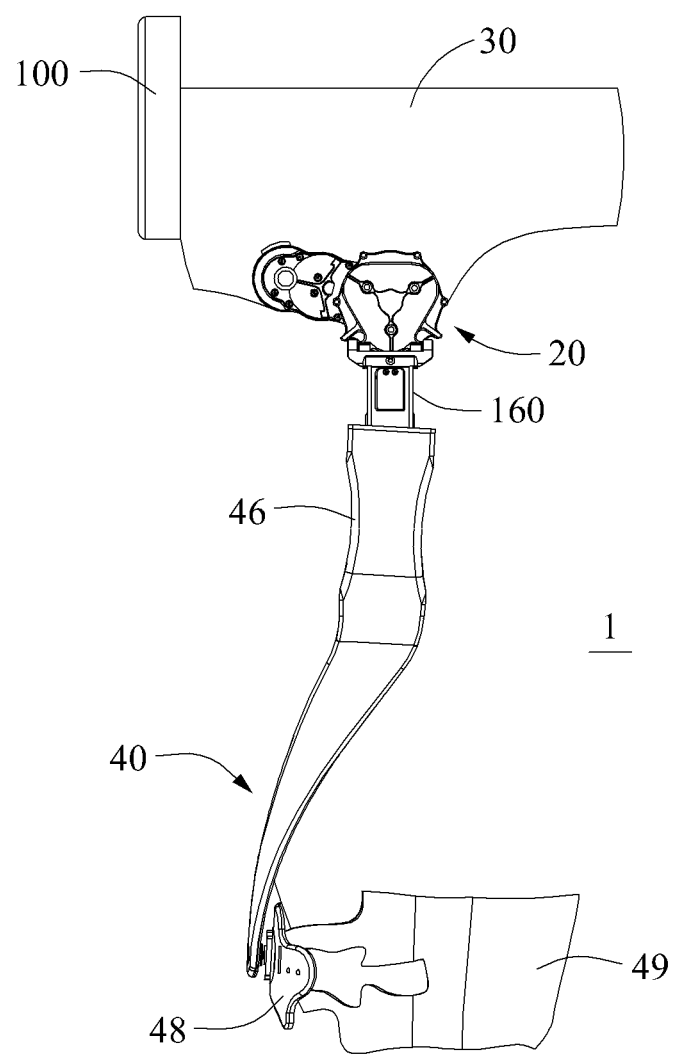
FIG. 1 is a side view of a motion assistance apparatus, according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. The same reference numbers indicate the same components throughout the specification. Also, in the description of embodiments, detailed description of well-known related structures or functions will be omitted when it is deemed that such description will cause ambiguous interpretation of the example embodiments.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components, regions, layers and/or sections, these elements, components, regions, layers and/or sections should not be limited by these terms. Each of these terminologies is not used to define an essence, order or sequence of a corresponding component but used merely to distinguish the corresponding component from other component(s). These terms are only used to distinguish one element, component, region, layer or section from another element, component, region, layer or section. Thus, a first element, component, region, layer or section discussed below could be termed a second element, component, region, layer or section without departing from the teachings of example embodiments.

It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

Various example embodiments will now be described more fully with reference to the accompanying drawings in which some example embodiments are shown. In the drawings, the thicknesses of layers and regions are exaggerated for clarity.

FIG. 1 is a side view of a motion assistance apparatus, according to at least one example embodiment. Referring to FIG. 1, a motion assistance apparatus 1 may be worn by a user to assist a motion of the user.

The user may be, for example, a human, an animal, or a robot. However, example embodiments are not limited thereto. Although FIG. 1 illustrates a case in which the motion assistance apparatus 1 is configured to assist a motion of a thigh of the user, the motion assistance apparatus 1 may be configured to assist a motion of another part of an upper body, for example, a hand, an upper arm, and a lower arm of the user, or a motion of another part of a lower body, for example, a foot, and a calf of the user. Thus, the motion assistance apparatus 1 may assist a motion of a part of the user.

The motion assistance apparatus 1 includes a fixing module 30, a supporting module 40, a driving module 20, and a battery pack 100 configured to supply a power to the driving module 20. The driving module 20 may be disposed on a member of the user such as, for example, a hip joint of the user to drive a joint portion of the motion assistance apparatus 1. Two driving modules, for example, the driving module 20, may be disposed on left and right hip joints to assist rotary motions of the left and right hip joints, respectively.

The fixing module 30 may be attached to the user. The fixing module 30 may be in contact with at least a portion of an outer surface of the user, and may be provided to cover the outer surface of the user. The fixing module 30 may include a curved surface to be in contact with the user. For example, the fixing module 30 may be attached to one side of a waist of the user.

The supporting module 40 may further include a supporting frame 46. The supporting frame 46 coupled to a connecting member 160 may be configured to rotate in a direction in which the connecting member 160 is rotated by the driving module 20. The supporting module 40 may include a pressurizing member 48 connected from the supporting frame 46, and a supporting member 49.

The pressurizing member 48 may be connected to one side of the supporting frame 46. For example, the pressurizing member 48 may be disposed on one side of a leg of the user to pull or push a thigh of the user. The pressurizing member 48 may be disposed on a front surface of the thigh of the user.

The supporting member 49 may be connected to one side of the pressurizing member 48. For example, the supporting member 49 may be disposed to cover a circumference of at least a portion of the thigh of the user, thereby preventing a separation of the thigh of the user from the supporting frame 44. The supporting member 49 may be disposed on an opposite side of the pressurizing member 48 from the thigh of the user.

A torque generated by the driving module 20 may be transmitted to the supporting module 40 through the connecting member 160. The torque transmitted through the supporting module 40 may be used to lift the thigh of the user through the pressurizing member 46, thereby assisting a motion of the user.

In at least one example embodiment, the battery pack 100 may be disposed on various parts of the user such as, for example, the back, the waist, and a leg. In a case of the motion assistance apparatus 1 worn to a waist, the battery pack 100 may be disposed on the waist. Unlike the back, the waist may move up and down and may make a left and right motion and a large rotative motion in a rolling direction for a central movement, thereby increasing a degree of energy harvesting.

Figure 2:
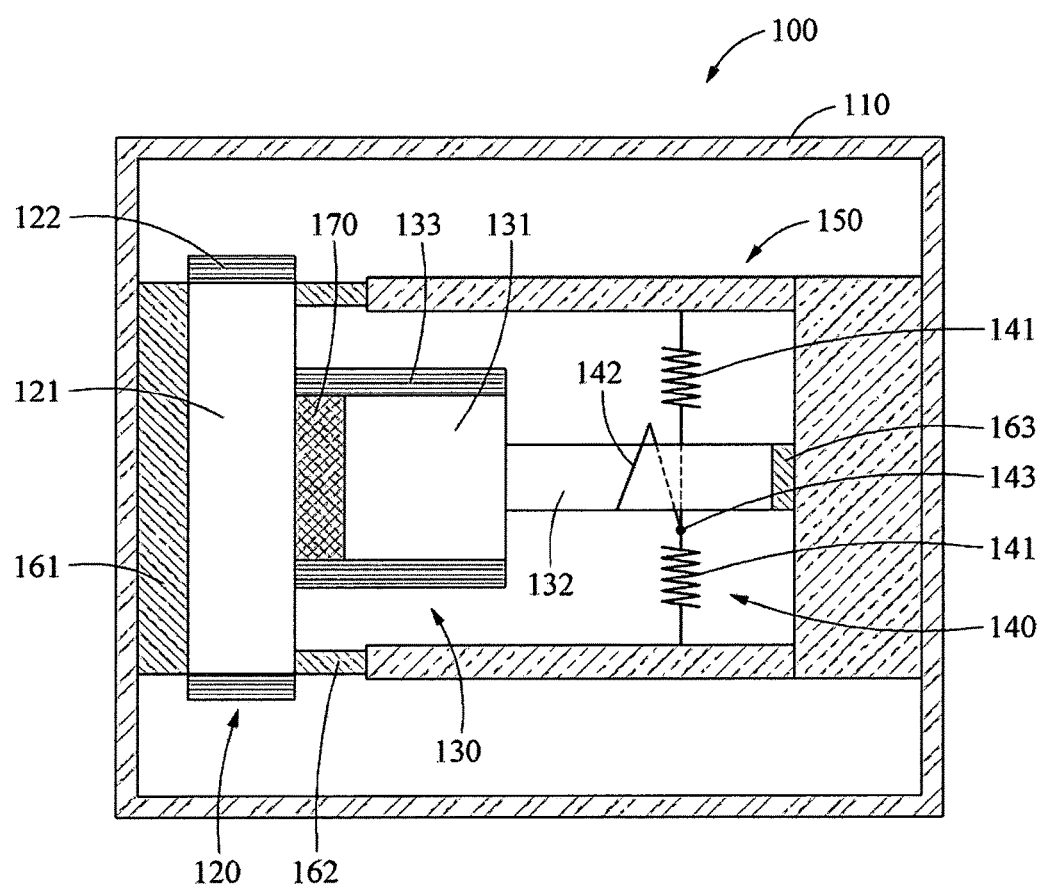
FIG. 2 is a cross-sectional view of a battery pack according to at least one example embodiment.

FIG. 2 is a cross-sectional view of the battery pack 100 according to at least one example embodiment. A case 110 may be formed in various shapes such as, for example, a rectangular parallelepiped shape, a cylindrical shape, or a conical shape. A battery 120 which is relatively movable with respect to the case 110, is included inside the case 110.

A generator 130, a charging circuit 170, and the battery 120 are sequentially arranged. The charging circuit 170 disposed between the generator 130 and the battery 120 is disposed on one inside surface of the case 110. The charging circuit 170 charges the battery 120 by a power produced in the generator 130.

The battery 120, the charging circuit 170, and the generator 130 are arranged in a stacking configuration, or are attached as a single object. Therefore, the battery 120, the charging circuit 170, and the generator 130 may be moved to a substantially identical direction as a single object in the case 110.

The generator 130 includes a generation axis 132 and a generation main body 131 to generate a power when the generation axis 132 is rotated. The generation axis 132 may be protruded from a center of the generation main body 131. The generation axis 132 may be in contact with an inside surface of the case 110 or may extend to be in contact with the inside surface of the case 110.

A rotation member 140 may be connected to the generation axis 132, and the rotation member 140 may act as a torque enabling the generation axis 132 to be rotatable when the battery 120 and the generator 130 are moved. The rotation member 140 may include the connecting body 142, one end of which is connected to the generation axis 132 and another end is to be spaced apart from a center of the generation axis 132, and elastic bodies 141 connected to the other end of the connecting body 142 and the supporting member 150.

The connecting body 142 may be a torsion spring extended by coiling around the generation axis 132 from the center of the generation axis 132. In addition, the elastic bodies 141 may be provided in a plurality of coil springs. A torsion spring and a coil spring may be connected at contact point 143. The torsion spring is connected to the generation axis 132 from the contact point 143, and the coil spring is connected to the supporting member 150.

The case 110 may include the supporting member 150 to support the battery 120 by pressing an upper surface of the battery 120 in order to restrict a movement of the battery 110 in a direction of the generation axis 132. The supporting member 150 may be, for example, integrated with the case 110, and may be disposed on an opposite side of the battery 120.

A lower surface of the battery 120 may be in contact with the case 110 and the upper surface of the battery 120 may be in contact with the supporting member 150. The supporting member 150 may restrict the movement of the battery 120, so that the supporting member 150 is not moved in the direction of the generation axis 132 by pressing the upper surface of the battery 120.

The supporting member 150 may have a shape of a cup or a container in order to surround the generator 130. The generator 130 may be relatively movable with respect to the supporting member 150 or the case 110 in a space formed by the supporting member 150.

When the battery 120 and the generator 130 are moved in the case 110, a generation main body-cushioning material 133 may be provided along an outside of the generation main body 131, since an impact occurs in the generation main body 131 when the generation main body 131 is in contact with the supporting member 150. Also, when the battery 120 and the generator 130 are moved in the case 110, a battery-cushioning material 122 may be provided outside of the battery main body 121, since an impact occurs between the battery 120 and the case 110.

In the battery pack 100, several bearings such as, for example, three bearings, may be provided. A first bearing 162 is disposed between the upper surface of the battery 120 and the supporting member 150, thereby reducing a frictional force occurring when the battery 120 is moved on a vertical plane relative to the direction of the generation axis 132. A second bearing 161 may be provided. The second bearing 161 is disposed between the case 110 and the lower surface of the battery 120, thereby reducing a frictional force. In addition, a third bearing 163 may be further provided. The third bearing 163 is disposed between an end of the generation axis 132 and the supporting member 150, thereby reducing a frictional force occurring when the generation axis 132 is in contact with the supporting member 150. Detailed descriptions of the first bearing 161, the second bearing 162, and the third bearing 163 will be provided with reference to FIG. 5 below.

Figure 3:
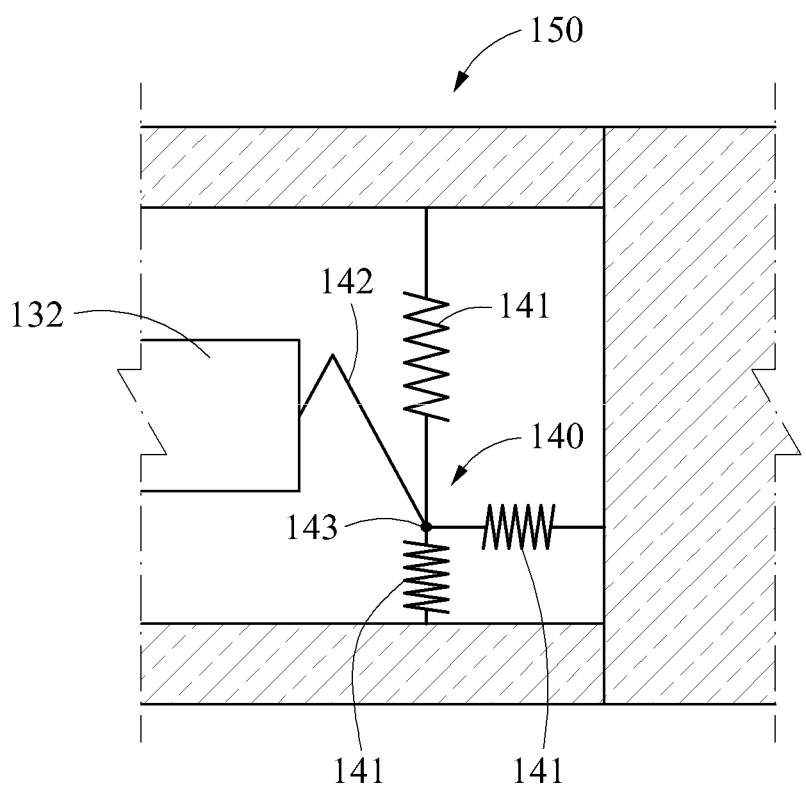
FIG. 3 is a cross-sectional view in which a portion of a generation axis of a battery pack is magnified, according to at least one example embodiment.

FIG. 3 is a cross-sectional view in which a portion of the generation axis 132 of the battery pack 100 is magnified, according to at least one example embodiment. FIG. 3 illustrates a configuration where the generation axis 132 is not in contact with the supporting member 150.

The generation axis 132 and the rotation member 140 are included in an empty space formed by the supporting member 150, and the rotation member 140 is provided between the generation axis 132 and the supporting member 150.

In the rotation member 140, the connecting body 142 is a torsion spring and the elastic bodies 141 in a coil spring are disposed at the contact point 143, and the connecting body 142 is connected between the contact point 143 and the generation axis 132. The elastic bodies 141 connect an inner side surface of the supporting member 150 with the contact point 143. A connecting spring 144 may be provided on an inner upper surface of the supporting member 150 and the contact point 143 in order to prevent the contact point 143 from moving toward the generation axis 132.

One end of the connecting body 142 is connected to about the center of the generation axis 132, and another end is connected to the contact point 143 at a position to be spaced apart from the center of the generation axis 132. The connecting body 142 is extended and spirally coiled in a direction of a rotation axis of the generation axis 132. The connecting body 142 has a shape, for example, which diameter gradually increases.

Figure 4A:
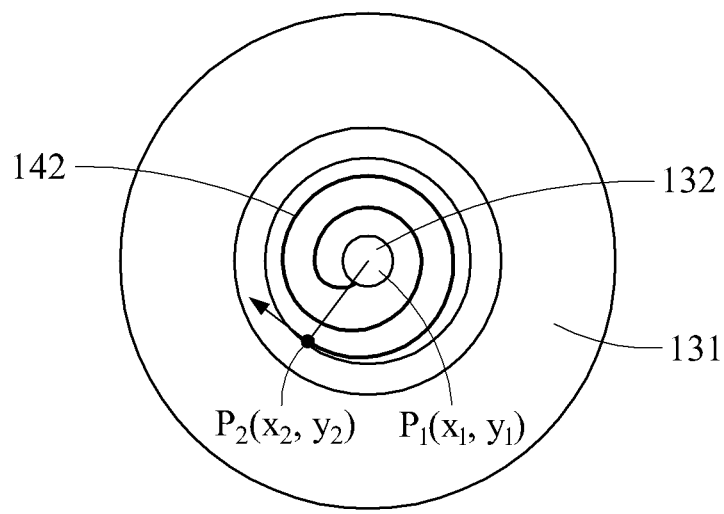
FIGS. 4A through 4C are top views of a generation axis and a rotation member of a battery pack, according to at least one example embodiment.
Figure 4B:
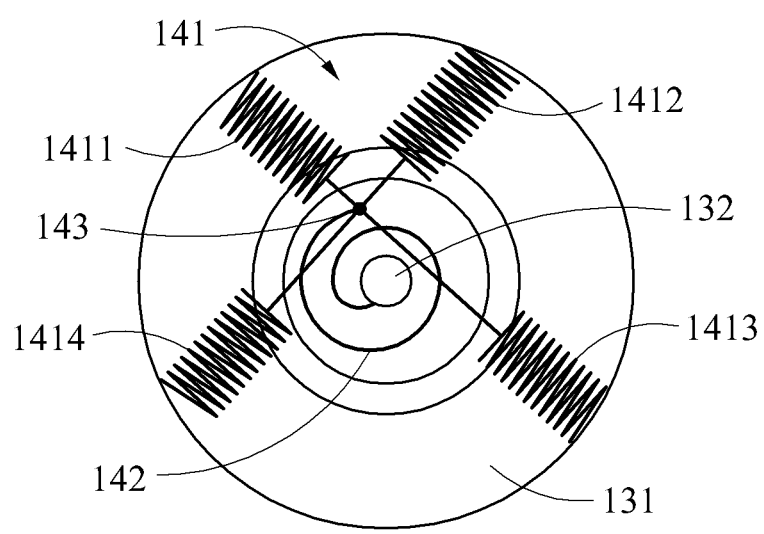
Figure 4C:
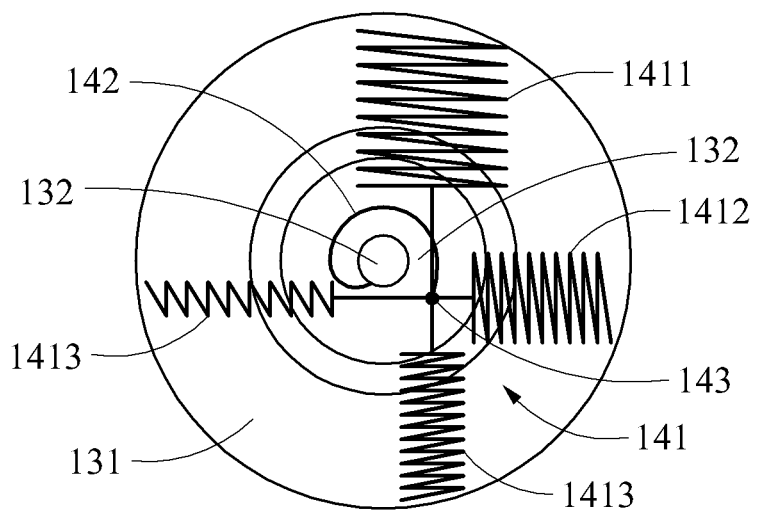

FIGS. 4A through 4C are top views of the generation axis 132 and the rotation member 140 of the battery pack 100, according to at least one example embodiment.

FIG. 4A illustrates the connecting body 142 in a torsion spring type connected to the center of the generation axis 132. When a spring constant of the connecting body 142 in the torsion spring type is K, a torque received by the connecting body 142 at θ position may be τ=−Kθ. Since a relationship of $$\theta = \tan^{-1}\frac{x2 - x1}{y2 - y1}$$

is obtained, τ is not generated at a point at which θ is nπ/2 (n=0,1, . . . ).

Accordingly, asymmetrically disposing P1 and P2 is appropriate. Even when the connecting body 142 in a simple torsion spring type is used as illustrated in FIG. 4A, P1 and P2 are asymmetrically disposed and a movement in a straight line and a rotative movement of the battery 120 generate the torque when θ is not positioned at nπ/2 in a steady state, thereby generating electricity by a rotation of the generation axis 132.

FIGS. 4B and 4C illustrate the connecting body 142 in the torsion spring type connected to the elastic bodies 141 in a coil spring type. The connecting body 142 and the elastic bodies 141 are connected based on the contact point 143.

A plurality of elastic bodies 1411, 1412, 1413, and 1414 may be radially disposed based on the contact point 143. Opposite end portions of the elastic bodies 141 connected to the contact point 143 may be connected to the supporting member 150 or the inner side surface of the case 110.

The elastic bodies 141 may be provided in four coil springs, and at least one of the elastic bodies 1411, 1412, 1413, and 1414 may have a different spring constant from the remaining elastic bodies. The elastic bodies 1411, 1412, 1413, and 1414 may be substantially orthogonal based on another end of the contact point 143 in a balanced condition.

For example, two methods of asymmetrically disposing the elastic bodies 1411, 1412, 1413, and 1414 may be provided. FIG. 4B illustrates an example of a method of generating an asymmetric shape by varying a length of the coil spring having a same spring constant. FIG. 4C illustrates an example of a method of using coil springs having different spring constants.

To adjust the length of the coil spring may have limitation due to a connection relationship between the supporting member 150 and the case 110. Thus, using different types of springs is helpful to differentiate the spring constants of each coil spring.

Figure 5A:
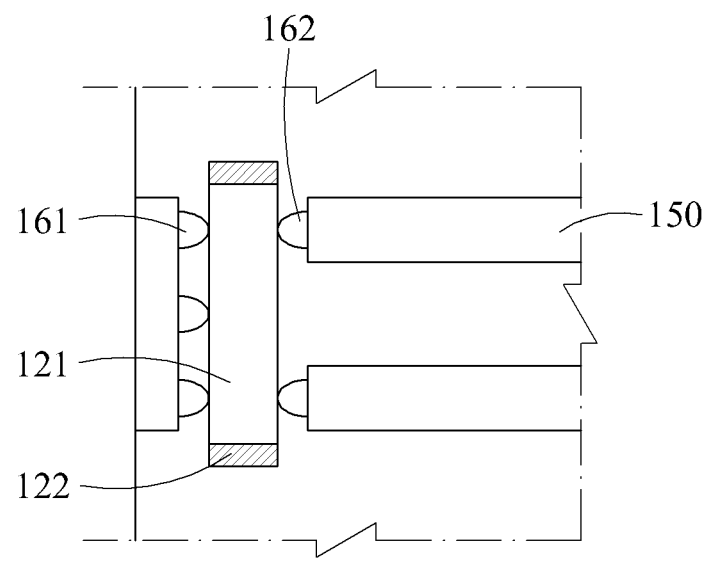
FIGS. 5A through 5C are cross-sectional views of a first bearing and a second bearing of a battery pack, according to at least one example embodiment.
Figure 5B:
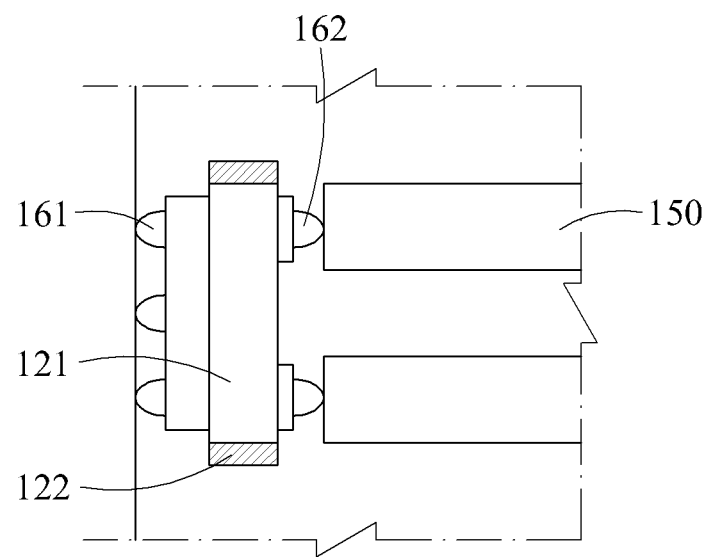
Figure 5C:
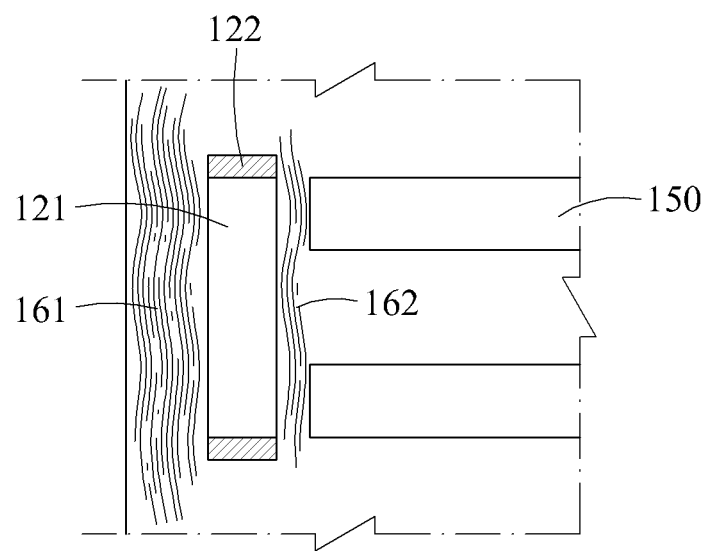

FIGS. 5A through 5C are cross-sectional views of the first bearing 161 and the second bearing 162 of the battery pack 100, according to at least one example embodiment. For ease of description, the shape of the generator 130 is omitted.

FIG. 5A illustrates a case in which bearings are not coupled with the battery main body 121. The bearing 162 is attached to an end of the supporting member 150. When the battery main body 121 is moved, the battery main body 121 is not in direct contact with the supporting member 150 because of the presence of the first bearing 162, such that the battery 120 is easily movable.

Also, the second bearing 161 may be attached to the inner surface of the case 110 and in contact with the battery main body 121. Since a substantially entire lower surface of the battery main body 121 is in contact with the inner surface of the case 110, an area in which the second bearing 161 is disposed may be larger than an area of the lower surface of the battery main body 121, such that the battery main body 121 is substantially fully supported by the second bearing 161.

The first bearing 162 and the second bearing 161 may be a roller bearing, a ball bearing, or any types of bearing structure.

FIG. 5B illustrates a case in which bearings are coupled with the battery main body 121. The first bearing 162 may be disposed on the upper surface of the battery main body 121, and the second bearing 161 may be disposed on the lower surface of the battery main body 121.

Since the generator 130 illustrated in FIG. 1 is on the upper surface of the battery main body 121, the first bearing 162 may be on a boundary portion of the upper surface of the battery main body 121, thus saving space for disposing the generator 130.

FIG. 5C illustrates a case in which a lubricant is used instead of the first bearing 162 and the second bearing 161. The lubricant and a bearing may be simultaneously or contemporaneously used. When a liquid lubricant is used, the liquid lubricant may sometimes flow in the generator 130, thereby causing a breakdown. Thus, using a solid lubricant is advantageous. When a lubricant is used, continuously supplying a lubricant may be advantageous such that the lubricant does not dry.

FIGS. 6A through 7B illustrate a process during an up and down movement of the battery pack 100. In a case of a user wearing the motion assistance apparatus 1 illustrated in FIG. 1, the event illustrated in FIGS. 6A and 6B may occur when the user, for example, lifts their waist. Conversely, a situation illustrated in FIGS. 7A and 7B may occur when the user, for example, lowers their waist towards the floor.

Figure 6A:
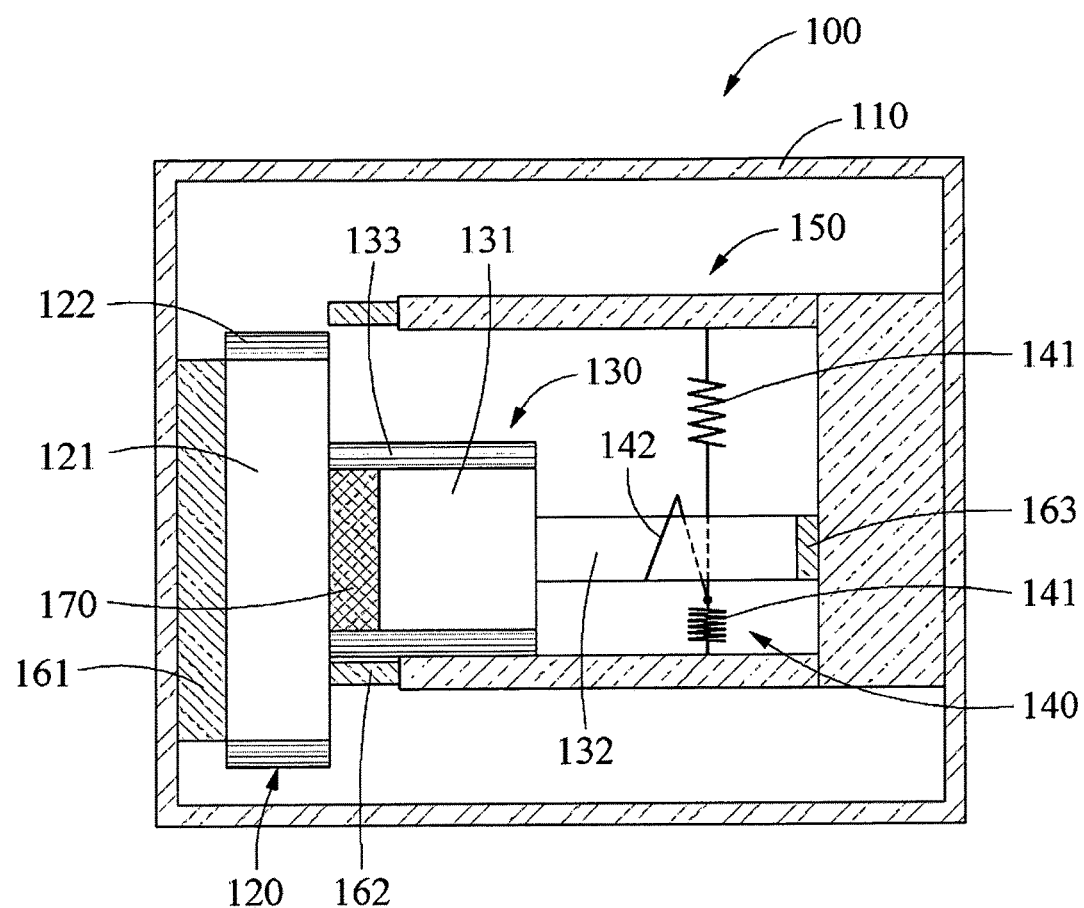
FIGS. 6A and 6B are views of a battery pack moving in an upward direction, according to at least one example embodiment.
Figure 6B:
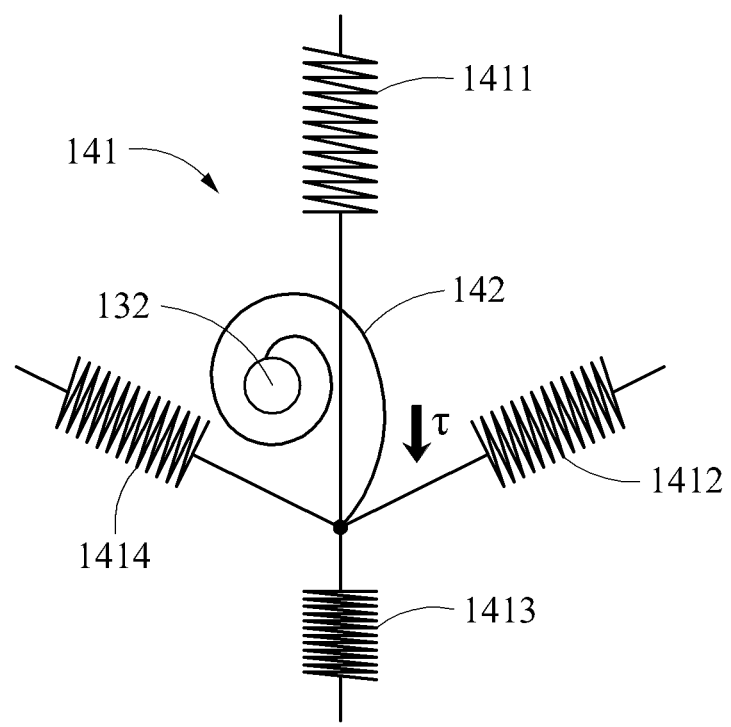

Referring to FIGS. 6A and 6B, when the user raises the battery pack 100, the generator 130 and the battery 120 are moved relatively downward with respect to the case 110 due to the law of inertia.

The plurality of elastic bodies 1411, 1412, 1413, and 1414 in the coil spring type may act a torque in a clockwise direction with respect to the generation axis 132 by the connecting body 142 in the torsion spring type. As time elapses, a coil spring may act as a torque in an anticlockwise direction with respect to the generation axis 132 by a restoring force of the coil spring.

While the torque is being generated, the generation axis 132 may be rotated to produce a power in the generation main body 131, and the produced power may be stored in the battery 120 by the charging circuit 170.

Figure 7A:
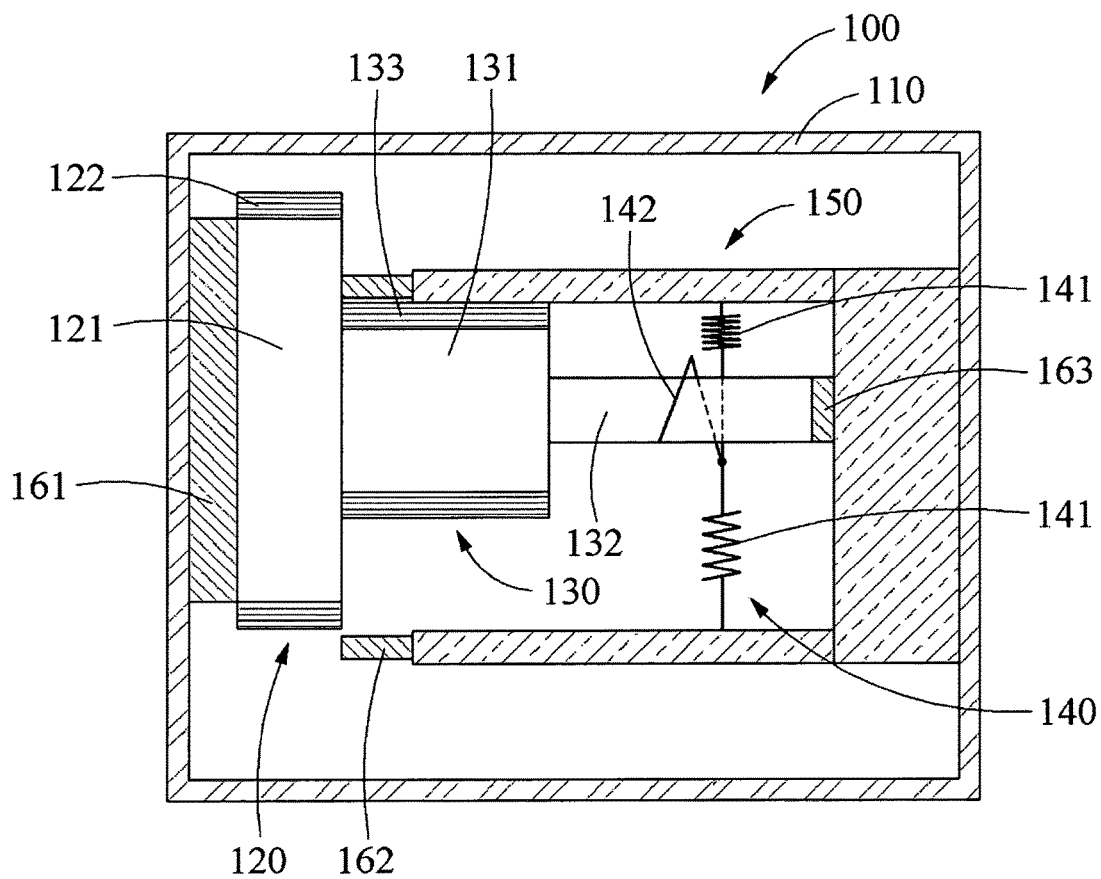
FIGS. 7A and 7B are views of a battery pack moving in a downward direction, according to at least one example embodiment.
Figure 7B:
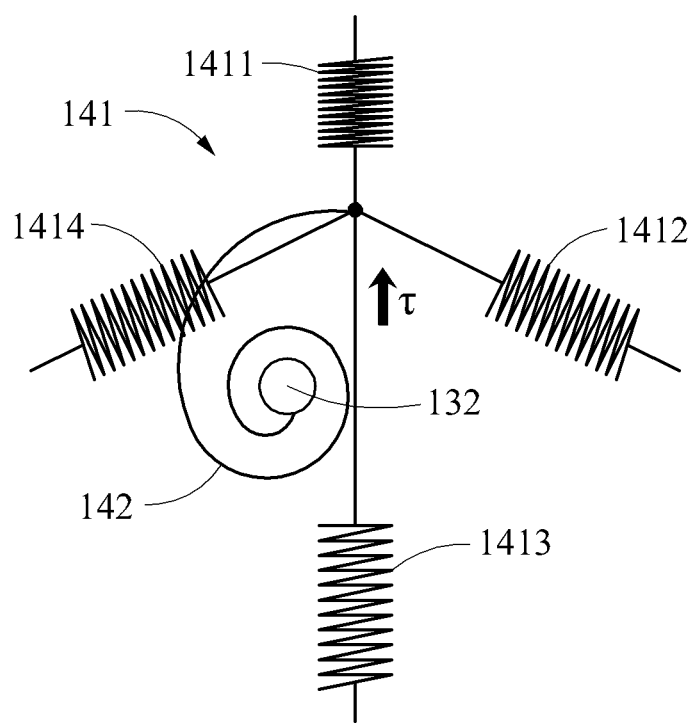

Referring to FIGS. 7A and 7B, when the user lowers the battery pack 100, the generator 130 and the battery 120 are moved relatively upward with respect to the case 110 due to the law of inertia.

The plurality of elastic bodies 1411, 1412, 1413, and 1414 in the coil spring type may be dragged downward when the user lowers the battery pack 100. The plurality of elastic bodies 1411, 1412, 1413, and 1414 in the coil spring type may act as the torque in an counter-clockwise direction with respect to the generation axis 132 by the connecting body 142 in the torsion spring type. Also, as time elapses, a coil spring may act as the torque in a clockwise direction with respect to the generation axis 132 by the restoring force of the coil spring.

Figure 8:
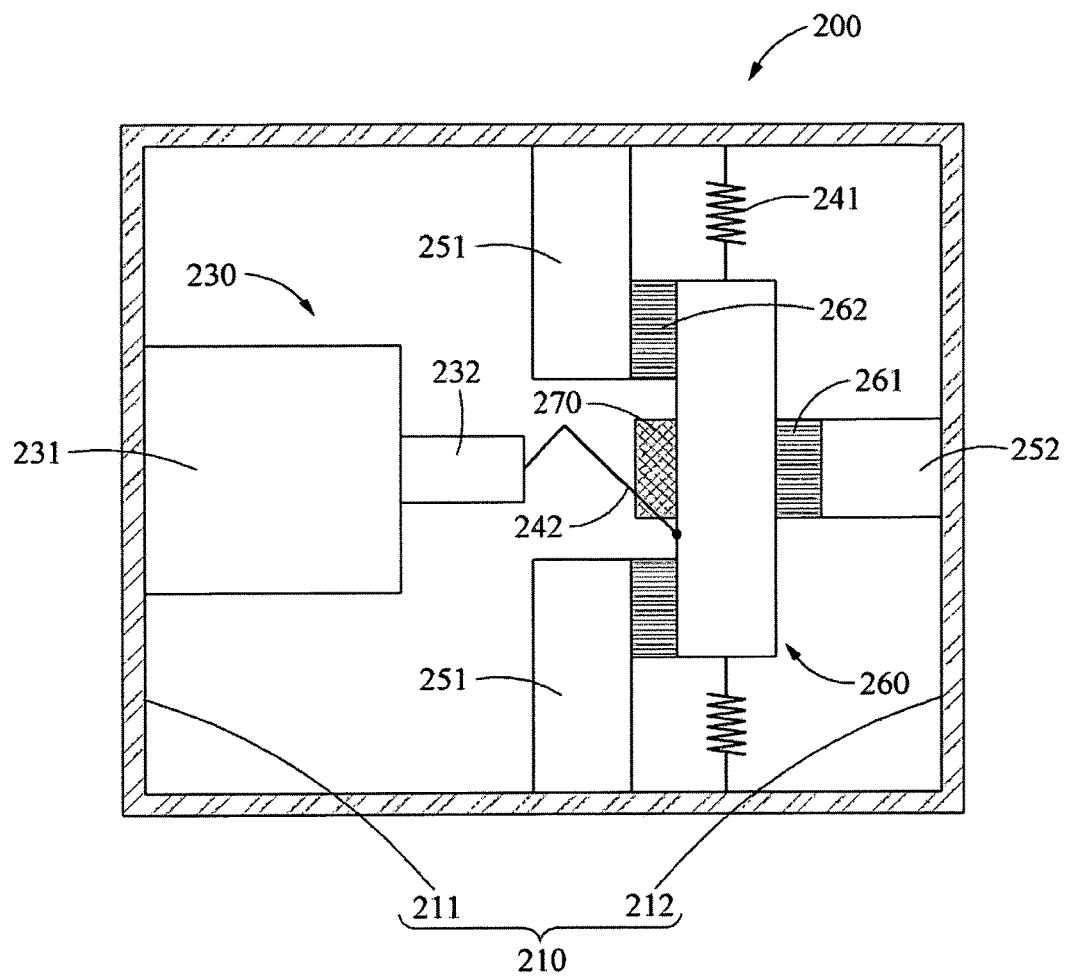
FIG. 8 is another cross-sectional view of a battery pack according to at least one example embodiment.

FIG. 8 is another cross-sectional view of a battery pack 200 according to at least one example embodiment. In the battery pack 200, a generator 230 is to be spaced apart from a battery 260. A generator 230 comprises a generator body 231, and the generator body 231 is fixed to a plane 211.

The battery pack 200 includes a case 210 including two planes 211 and 212 facing each other, a generator 230 attached to the plane 211 among two planes 211 and 212 of the case 210 and including a generation axis 232, the battery 260 disposed on the plane 212, which is different from the plane 211 on which the generator 230 is located and is relatively movable with respect to the case 210, a connecting body 242 connecting a center of the generation axis 232 and the battery 260 at an off-center position, and an elastic body 241 connecting the case 210 and the battery 260. Furthermore, the connecting body 242 may act as a torque enabling the generation axis 232 to be rotatable when the battery 260 is moved.

The generation axis 232 and the battery 260 are connected by the connecting body 242 in a torsion spring type. One end of the connecting body 242 is connected to the center of the generation axis 232 and another end of the connecting body 242 is connected to one surface of the battery 260 at the off-center position of the generation axis 232.

On a side surface of the battery 260, a plurality of elastic bodies, for example, the elastic body 241, in a coil spring type may be provided. The elastic body 241 may connect the battery 260 to an inner side surface of the case 210.

A first supporting member 251 in contact with an upper surface or a lower surface of the case 210 may be provided in order to restrict a movement of the battery 260 in the direction of the generation axis 232. The first supporting member 251 may be attached to the inner side surface of the case 210 and formed in a plate having a hole in a center that enables the generation axis 232 to pass through.

The first supporting member 251 and the second supporting member 252 may be disposed at both sides of the battery 260. The second supporting member 252 may be configured to adjust an aperture between the battery 260 and the generator 230.

Between the battery 260 and the first supporting member 251, a first bearing 262 to reduce a frictional force between the battery 260 and the first supporting member 251, and a second bearing 261 to reduce a frictional force between an inside surface of the case 210 and the battery 260, may be provided. When the inside surface of the case 210, the battery 260, and the second supporting member 252 are in direct contact with each other, the second bearing 261 may reduce the frictional force between the battery 260 and the second supporting member 252.

A charging circuit 270 may be disposed between one surface of the battery 260 and the connecting body 242. The generation axis 232 and the battery 260 may be electrically connected by the conductive connecting body 242. The charging circuit 270 may charge the battery 260 by a power produced in the generator 230.

Since the generator 230 is attached, the battery 260 may be relatively movable with respect to the generator 230. When the battery pack 200 is moved, the battery 260 is swayed, thereby generating a torque in the generation axis 232 of the generator 230 by the connecting body 242. Here, the elastic body 241 may provide a restoring force so that the battery 260 does not stop moving by turning relatively to the axis of the generation axis 232.

As describe above, according to at least one example embodiment, it is possible to reduce the inconvenience for a user to connect the battery pack to a charger, or to separate the battery pack for charging, by increasing the use time of the walking assistance apparatus when the battery pack having the energy harvesting characteristic discussed above is used. Also, it is possible to continue to use the walking assistance apparatus by charging the battery pack by shaking a waist or dancing without connecting the battery pack to the charger even when the battery pack is completely discharged.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A battery pack comprising:
  a case;
  a battery in the case and movable with respect to the case;
  a generator attached to the battery and including a generation axis; and
  a rotation member connected to the generation axis,
  wherein the rotation member is configured to act as a torque enabling the generation axis to be rotatable when the battery is in motion.

2. The battery pack of claim 1, wherein the rotation member comprises:
  a connecting body, one end of which is connected to the generation axis, and an other end of which is apart from a center of the generation axis; and
  a plurality of springs connected to the other end of the connecting body and to the case.

3. The battery pack of claim 2, wherein the connecting body is a torsion spring extended by coiling around the generation axis from the center of the generation axis.

4. The battery pack of claim 2, wherein a plurality of elastic bodies are radially located with respect to the other end of the connecting body.

5. The battery pack of claim 4, wherein at least one of the plurality of elastic bodies has a different spring constant from spring constants of remaining ones of the plurality of elastic bodies.

6. The battery pack of claim 2, wherein an elastic body is provided in four coil springs, and the four coil springs are substantially orthogonal with respect to the other end of the connecting body in a balanced condition.

7. The battery pack of claim 1, wherein the case comprises a supporting member configured to support the battery and restrict a movement of the battery in a direction of the generation axis.

8. The battery pack of claim 7, wherein the supporting member is configured to surround the generator, and the generator is relatively movable in the supporting member.

9. The battery pack of claim 7, wherein one surface of the battery is in contact with the case, and another surface of the battery is in contact with the supporting member.

10. The battery pack of claim 7, further comprising:
  a first bearing between the battery and the supporting member, the first bearing being configured to reduce a frictional force occurring when the battery is moved on a vertical plane relative to the direction of the generation axis; and
  a second bearing between the case and the battery.

11. The battery pack of claim 10, further comprising:
  a third bearing between the generation axis and the supporting member, the third bearing being configured to reduce a frictional force occurring when the generation axis is in contact with the supporting member.

12. A battery pack comprising:
a case including two planes facing each other;
a generator attached to a first one of the two planes and including a generation axis;
a battery on a second one of the two planes and movable with respect to the case;
a connecting body configured to connect a center of the generation axis and the battery at an off-center position; and
an elastic body configured to connect the case with the battery,
wherein the connecting body is configured to act as a torque enabling the generation axis to be rotatable when the battery is moved.

13. The battery pack of claim 12, further comprising:
a supporting member in contact with one surface of the battery, the supporting member being configured to restrict a movement of the battery in a direction of the generation axis.

14. The battery pack of claim 13, further comprising:
a first bearing between the battery and the supporting member, the first bearing being configured to reduce a frictional force between the battery and the supporting member; and
a second bearing between the second one of the two planes of the case and the battery.

15. A motion assistance apparatus comprising:
a battery pack including a battery movably inserted inside a case, a generator attached to the battery and including a generation axis, and a rotation member configured to connect the generation axis with the case;
a driving module configured to be supplied in power by the battery pack;
a fixing module to which the driving module is attached, the fixing module configured to be attached to a user;
a supporting module configured to support a portion of a body of the user and to be driven by the driving module,
wherein the rotation member is configured to act as a torque enabling the generation axis to be rotatable when the battery is moved in response to a motion of the user wearing the motion assistance apparatus.

16. The motion assistance apparatus of claim 15, wherein the rotation member comprises:
a torsion spring, one first end of which is connected to the generation axis, and an other end of which is apart from a center of the generation axis; and
at least one coil spring connected to the other end of the torsion spring and to the case.

17. The motion assistance apparatus of claim 15, wherein the case comprises a supporting member configured to be in contact with one surface of the battery and support the battery in order to restrict a movement of the battery in a direction of the generation axis.

18. The motion assistance apparatus of claim 16, wherein a plurality of coil springs are provided, and at least one of the plurality of coil springs has a different spring constant from spring constants of remaining ones of the plurality of coil springs, and
a resultant force applied by the plurality of coil springs has a different direction from a direction that is parallel to the generation axis.

* * * * *